(12) United States Patent
Manhart

(10) Patent No.: US 10,856,829 B2
(45) Date of Patent: Dec. 8, 2020

(54) RECONSTRUCTING A THREE-DIMENSIONAL IMAGE DATA RECORD RECORDED WITH A BIPLANAR X-RAY DEVICE

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 119 days.

(21) Appl. No.: 16/219,361

(22) Filed: Dec. 13, 2018

(65) Prior Publication Data
US 2019/0192101 A1    Jun. 27, 2019

(30) Foreign Application Priority Data

Dec. 21, 2017   (DE) .......................... 10 2017 223 603

(51) Int. Cl.
*A61B 6/00* (2006.01)
*A61B 6/03* (2006.01)
*A61B 6/02* (2006.01)

(52) U.S. Cl.
CPC ............ *A61B 6/5258* (2013.01); *A61B 6/032* (2013.01); *A61B 6/4441* (2013.01); *A61B 6/486* (2013.01);
(Continued)

(58) Field of Classification Search
USPC ................................ 382/128, 131–132, 154
See application file for complete search history.

(56) References Cited

U.S. PATENT DOCUMENTS 7,050,844 B2 *  5/2006  Strobel ..................... A61B 6/12
600/424
7,263,157 B2 *  8/2007  Bruder ................... A61B 6/032
378/15
(Continued)

FOREIGN PATENT DOCUMENTS

DE   102006021372 B4   2/2010
DE   102015218596 A1   3/2017

OTHER PUBLICATIONS

Machine Translaion of Gerrman Office Action for German Application No. 102017223603 5, Oct. 9, 2018.*
(Continued)

*Primary Examiner* — Ishrat I Sherali
(74) *Attorney, Agent, or Firm* — Lempia Summerfield Katz LLC

(57) ABSTRACT

A three-dimensional image data record of an examination object is reconstructed from two-dimensional projection images recorded with a biplanar x-ray device. The biplanar x-ray device has two recording arrangements of x-ray emitter and x-ray detector pairs measuring projections displaced by an angle relative to one another. The projection images are simultaneous pairs of projection images recorded at the same time with the different recording arrangements. For the image-based, in particular rigid, registration of the recording arrangements with respect to one another for at least one part, preferably all, of the simultaneous pairs, a degree of consistency based on a redundancy in the projection data of the projection images is determined. A determination of the registration parameters describing the registration of the recording arrangements is carried out by minimizing a consistency metric determined by totaling the degrees of consistency in an optimization method.

20 Claims, 2 Drawing Sheets

(52) U.S. Cl.
CPC ............ *A61B 6/507* (2013.01); *A61B 6/5205* (2013.01); *A61B 6/027* (2013.01); *A61B 6/4014* (2013.01); *A61B 6/584* (2013.01)

(56) References Cited

U.S. PATENT DOCUMENTS

| | | | | |
|---|---|---|---|---|
| 7,806,589 | B2 * | 10/2010 | Tashman | A61B 5/1038 |
| | | | | 378/193 |
| 8,059,874 | B2 | 11/2011 | Pfister et al. | |
| 8,340,373 | B2 * | 12/2012 | Claus | G06T 11/006 |
| | | | | 378/4 |
| 8,879,814 | B2 * | 11/2014 | Wollenweber | A61B 6/032 |
| | | | | 382/131 |
| 10,039,512 | B2 * | 8/2018 | Elsasser | G01N 23/046 |
| 2007/0258639 | A1 * | 11/2007 | Pfister | G06T 11/006 |
| | | | | 382/154 |
| 2017/0086767 | A1 | 3/2017 | Elsässer | |
| 2020/0074700 | A1 * | 3/2020 | Kowarschik | A61B 6/504 |

OTHER PUBLICATIONS

Frysch, Robert, and Georg Rose. "Rigid motion compensation in interventional C-arm CT using consistency measure on projection data." International Conference on Medical Image Computing and Computer-Assisted Intervention. Springer, Cham, 2015.
German Office Action for German Application No. 102017223603.5, dated Oct. 9, 2018.
Wicklein, Julia, et al. "Image features for misalignment correction in medical flat-detector CT." Medical physics 39.8 (2012): 4918-4931.

* cited by examiner

RECONSTRUCTING A THREE-DIMENSIONAL IMAGE DATA RECORD RECORDED WITH A BIPLANAR X-RAY DEVICE

RELATED CASE

This application claims the benefit of DE 10 2017 223 603.5, filed on Dec. 21, 2017, which is hereby incorporated by reference in its entirety.

FIELD

The present embodiments relate to a method for reconstructing a three-dimensional image data record of an examination object from two-dimensional projection images recorded with a biplanar x-ray device. The biplanar x-ray device has two recording arrangements measuring projection directions displaced by an angle relative to one another, with in each case an x-ray emitter and an x-ray detector, and the projection images include simultaneous pairs of projection images recorded at the same time with the different recording arrangements. The present embodiments also relate to a biplanar x-ray device, to a computer program and to a non-transitory electronically readable data carrier.

BACKGROUND

It has already long been known in x-ray imaging, in particular in the field of medicine, to reconstruct higher dimensional image data records of an examination object, in particular of a patient, from lower dimensional projection images, in particular three-dimensional image data records from two-dimensional projection images. For this purpose, a plurality of reconstruction methods is known, for instance filtered back projection or iterative reconstruction (algebraic reconstruction). When the projection images are recorded with a single recording arrangement, it can be assumed that on account of the known movement of the recording arrangement all the projection images are registered with one another. Nonetheless, inaccuracies may occur during the reconstruction of the image data record if a patient movement occurs and/or a dynamic measurement is to take place, for instance a perfusion measurement.

In order to reduce such problems, it has already been proposed to increase the speed of rotation of the recording arrangement in order to reduce the influences of patient movements and/or dynamic processes within the examination object. However, this is associated with higher requirements on the mechanical stability of the recording arrangement or of a C-arm supporting the recording arrangement and with a potentially lower acceptance in the case of medical personnel and patients. Particularly with the C-arm CT used for instance during interventions (also referred to as "DynaCT"), further movement artifacts may occur, particularly in the case of patients in a critical state. For movement correction in such cases, an article by Robert Frysch and Georg Rose, "Rigid Motion Compensation in Interventional C-arm CT Using Consistency Measure on Projection Data", in: MICCAI 2015, Part I, LNCS 9349, pages 298-306, 2015, proposes the use of a geometric optimization algorithm, which is based on a degree of consistency of the projection data that reduces computationally complicated forward and backward projection steps in the optimization process. The degree of consistency described there is based on redundancies that occur in CT projection data of projection images, which redundancies manifest in the fundamental Grangeat's relation. An error measure, which describes the consistency of each combination of two projection images, can be derived therefrom. A totaling of the errors can be used to quantify the consistencies of a set of projection images. A rigid movement estimation for the individual images takes place on this basis.

To further reduce movement artifacts and/or to extend the application possibilities in dynamic measurements, it was meanwhile proposed to use the number of available recording arrangements in the case of biplanar x-ray devices in order to record projection images simultaneously and therefore to record a portion of the projection angular range to be covered by each of the recording arrangements. This enables shorter recording times. For instance, with a short scan (180° plus opening angle), a recording arrangement can acquire projection images of 0° to 100° and the other recording arrangement can acquire projection images of 100° to 200°, so that the recording time is reduced without increasing the maximum speed of rotation. Two subsets of projection images therefore emerge, namely one subset for each plane or each recording arrangement.

In order to be able to reconstruct an artifact-free volume from the image data record robustly from the two subsets, the geometries of the two recording arrangements are registered exactly with one another. The mechanical accuracy of the C-arms is however restricted specifically in the case of biplanar x-ray devices with C-arms, so that with each measurement the relative start point of the two recording arrangements may differ from one another. After each measurement, the recording geometries are therefore algorithmically registered rigidly with one another with the aid of the recorded projection images; this registration takes place in a computationally efficient, extremely robust manner for a protocol that is acceptable for clinical use, even in the case of a patient movement during the recording.

In order to register the recording arrangements and therefore the projection images of the subsets with one another, the six rigid registration parameters, three translation parameters and three rotation parameters, are estimated. In this context, it was proposed in an article by Julia Wicklein et al., "Image features for misalignment correction in medical flat-detector CT", Med. Phys. 39 (8), pages 4918-4931, 2012, to use image quality metrics of a reconstructed volume, for instance the entropy, variance and suchlike. The back-projection error is specifically proposed as a measure. In order to perform the registration, the image quality metric is optimized, requiring computationally complicated back projection steps within the scope of optimization. A further problem of the procedure proposed in this publication is that image quality metrics are also influenced by patient movement, thereby causing the robustness to suffer.

SUMMARY AND DETAILED DESCRIPTION

A more robust and less computationally complicated possibility, in particular influenced as little as possible by patient movement and dynamic processes, of registering subsets of projection images recorded with different recording arrangements of a biplanar x-ray device is specified.

A degree of consistency is based on a redundancy in the projection data of the projection images to be determined for the image-based registration of the recording arrangements with respect to one another for at least one part, preferably all, of the simultaneous pairs. A determination of the registration parameters describing the registration of the recording arrangements to take place in an optimization method is provided by minimizing a consistency metric determined by totaling the degrees of consistency.

Degrees of consistency with respect to pairs of projection images can also be used skillfully within the scope of the registration of recording arrangements with respect to one another. This takes advantage of the fact that with the simultaneous recording two projection images of a simultaneous pair are in each case recorded at least approximately at the same time so that patient movements and dynamic processes have no or at the most a minimal influence on the degree of consistency, essentially providing details relating to the rigid registration parameters. A consistency metric can therefore be determined by totaling the inconsistencies between the projection images of the simultaneous pairs recorded at the same time, wherein this consistency metric is robust with respect to patient movements and/or dynamic processes, for instance dynamic changes in density in the case of perfusion measurements.

Here the determination of the degrees of consistency and thus also the consistency metric can take place directly on the projection data, so that a computationally complicated backward projection and/or forward projection is avoided, and a computationally efficient registration is thus also enabled. Applying consistency metrics in a targeted fashion to projection images recorded substantially at the same time therefore overall enables a computationally efficient, robust and reliable registration of the subsets of projection images with respect to one another.

In a preferred embodiment, the degree of consistency introduced in the article by Robert Frysch and Georg Rose, already cited in the introduction, is used so that the embodiment can specifically provide that a degree of consistency based on the Grangeat's relation is used and/or an intermediate function is used to determine the degree of consistency, which is produced as a result of Radon transformation and differentiation of the projection images. The degree of consistency is determined from the intermediate function values containing the differences in redundant information. For the purpose of registering the recording arrangements with one another, it is therefore proposed firstly to determine an intermediate function by Radon transformation and differentiation of the recorded projection data, whereupon the six 3D registration parameters in the case of rigid registration are determined by optimizing a consistency metric. The consistency metric is calculated as the sum of the degrees of consistency of in each case two projection images recorded at the same time.

A particularly robust determination of the registration parameters is produced when the angle between the projection directions of the recording arrangements is selected to vary from 90°, particularly in the range of 95° to 105°, for instance as 100°. With the variation from 90°, the redundancies in the projection images increase advantageously, thereby permitting a more reliable registration. In general, the angle between the projection directions of the recording arrangements naturally remains constant during the recording of the projection images on account of a suitable mechanical and/or control-related coupling. A circular path is used expediently as a recording trajectory.

In a particularly preferred embodiment, provision can be made for the projection images to be recorded to cover a projection angular range of 180° plus the opening angle of the radiation field (radiation beam). The projection directions of the recording arrangements are offset by an angle of half of the extent of the projection angular range, and each recording arrangement in each case records projection images covering half of the projection angular range in each case. With a short scan of this type, each of the two recording arrangements can therefore assume half of the projection angle interval to be covered and record corresponding subsets of projection images, which are then registered with one another. For instance, with a projection angle interval of 200° to be covered, an offset by 100° results, wherein one of the recording arrangements records projection images in the range of 0° to 100°, the other at the same time in the range of 100° to 200°. Incidentally, an offset of the projection directions that differs from 90° is therefore also naturally provided and advantageously increases the number of existing redundancies.

The method can also be used particularly advantageously if a biplanar x-ray device with the C-arm supporting the recording arrangements is used. Mechanical inaccuracies that involve a requirement for a robust and reliable registration may result specifically in respect of C-arms.

The present embodiments can also be used particularly advantageously when the projection images are recorded within the scope of a dynamic measurement, in particular a perfusion measurement, and/or a measurement susceptible to patient movement. On account of the projection images being able to be combined to form simultaneous pairs of projection images recorded at the same time, variations owing to the not yet provided registration of patient movements and/or dynamic processes in the examination object are decoupled so that a reliable registration can take place in spite of their occurrence.

In a preferred development, provision can be made in this context for the degree of consistency of the projection images of the two recordings registered by the registration parameters also additionally to be used for movement correction and/or dynamic analysis. If a movement correction is to take place, for instance, the concept underlying the registration can also be applied to the (then registered) projection images, as is described in the cited article by Robert Frysch and Georg Rose, for instance.

In addition to the method, a biplanar x-ray device has two recording arrangements measuring projection directions displaced by an angle relative to one another, with in each case an x-ray emitter and an x-ray detector and a control device that is configured to carry out the method. All the embodiments relating to the method can be transferred analogously to the biplanar x-ray device, with which the cited advantages can therefore also be obtained. In particular, the recording arrangements are supported by C-arms here. Even when the angle between the projection directions of the recording arrangements typically remains constant during a measurement, it is absolutely conceivable to provide adjusting device, by which the offset angle can be set to different values, for instance with different, given opening angles of the radiation field and therefore different projection angle intervals to be covered in the case of short scans and suchlike. Such adjusting devices are typically also used if an in particular minimally invasive intervention is to be monitored, for instance, and optimal projection directions are to be freely selectable with fluoroscopy recordings to be measured simultaneously.

For instance, a computer program can be loaded directly into a memory of a computing device, in particular a control device of a biplanar x-ray device and includes a program or stored instructions to perform the acts of the method when the computer program is executed in the computing device (e.g., executed by a processor). The computer program can be stored on a non-transitory electronically readable data carrier, which therefore includes electronically readable control information stored thereupon. The computer program is embodied on the medium such that the instructions carries out the method when the data carrier is used in a computing device, in particular a control device of a biplanar x-ray device. The data carrier may preferably be a non-transient data carrier, in particular a CD-ROM.

BRIEF DESCRIPTION OF THE DRAWINGS

Further advantages and details result from the exemplary embodiments described below and with the aid of the drawing, in which.

DETAILED DESCRIPTION OF THE PREFERRED EMBODIMENTS

An exemplary embodiment is shown in more detail below, in which a short scan of an examination area of a patient is carried out using a biplanar x-ray device. The biplanar x-ray device has two recording arrangements, each with an x-ray emitter and an x-ray detector that are supported by a C-arm in each case. The angular position of the C-arms relative to one another and thus the angle of the projection directions of the recording arrangements can be adjusted by way of adjusting devices; the C-arms can be rotated jointly in order to record projection images at a fixed angular distance simultaneously.

Since the fan angle, in other words the opening angle of the radiation field, currently amounts to 20°, a projection angular range of 200° is overall to be covered for the short scan. The angle between the projection directions of the recording arrangements is set to 100°, so that the first recording arrangement records projection images in the projection angle interval of 0° to 100° and the second recording arrangement records projection images in the range of 100° to 200°. The recording is carried out in an act S1. The result is consequently two subsets 1, 2 of two-dimensional x-ray projection images, of which each has been recorded with another recording arrangement. In order to be able to reconstruct as high a quality three-dimensional image data record as possible, the spatial relationship between the recording arrangements must be known precisely, in other words the respective subsets 1, 2 have to be registered with one another. In the registration procedure proposed below, advantage is taken of the fact that each of the subsets 1, 2 currently has an equivalent number of projection images and each two of these projection images, which form a simultaneous pair, have (at least substantially) been recorded simultaneously, as symbolized by the double arrow 3. This means that the projection images of a simultaneous pair are, except for variations from the exact simultaneity which may occur and are not to be avoided, uninfluenced by movements of the patient and potentially dynamic processes, if perfusion imaging or another dynamic imaging is operated, for instance.

In an act S2, intermediate functions are determined with respect to the respective projection images. The functions are determined from the projection images as described in the cited article by Robert Frysch and Georg Rose, for instance, being Radon transform and differentiation.

In an act S3, a degree of consistency and therefore a consistency metric can be determined here from as a total of the individual degrees of consistency for all simultaneous pairs. The registration is now carried out by the consistency metric being minimized. The registration parameters are selected such that the consistency metric is minimal. In this way, any optimization methods known essentially in the prior art can ultimately be used and possibly boundary conditions taken into account.

Figure 1:
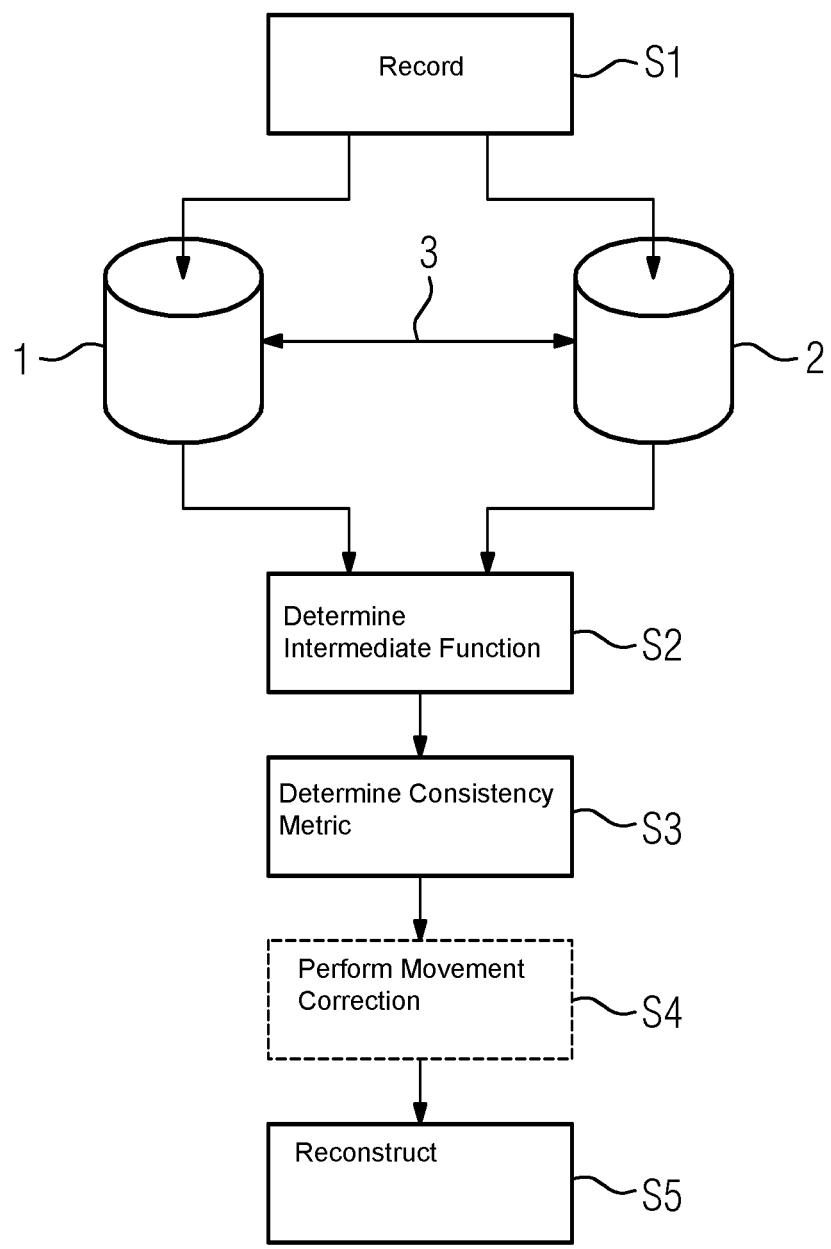
FIG. 1 shows a flow diagram of an exemplary embodiment.
Figure 2:
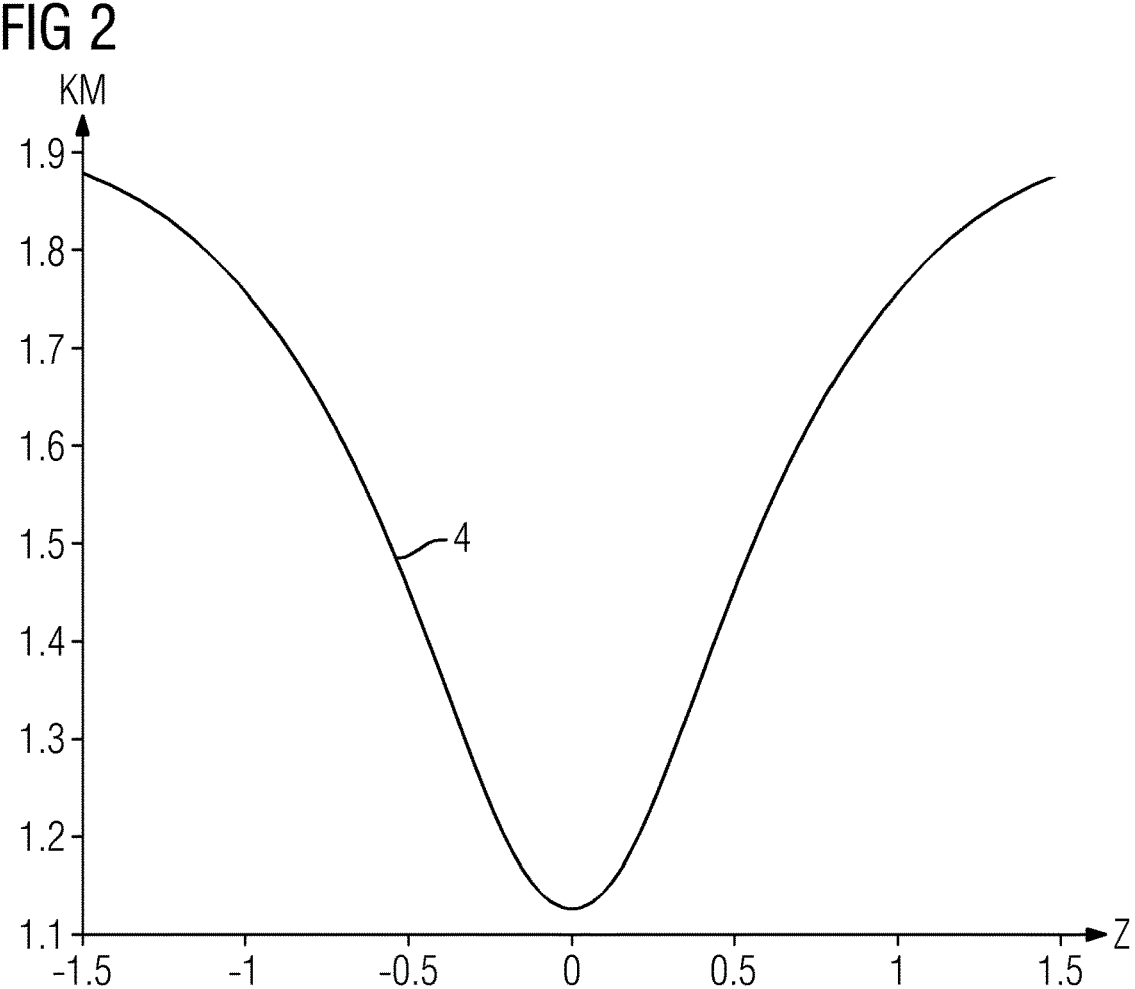
FIG. 2 shows an example course of the consistency metric with various axial displacements.

Using the example of one of these registration parameters, namely the out-of-plane displacement z of the recording arrangements relative to one another, FIG. 2 illustrates this optimization process more precisely. The degree of consistency KM against the axial displacement of the recording arrangements, referred to with z, is plotted as curve 4 and individual measuring points. A convex curve shape, which is particularly suited to the optimization, is produced. The optimum of the consistency metric is zero in terms of displacement. This clearly shows that a robust optimization is possible, since similar associations with respect to other registration parameters result.

The projection images of the subsets 1, 2, can be registered with one another using the registration rule obtained from the optimization method in act S3, whereupon consistency metrics can in turn be used in an optional act S4 in order to perform a movement correction, as is also described in the article by Robert Frysch and Georg Rose.

In an act S5, the final reconstruction of the three-dimensional image data record from the registered and possibly movement-corrected projection images then follows.

Figure 3:
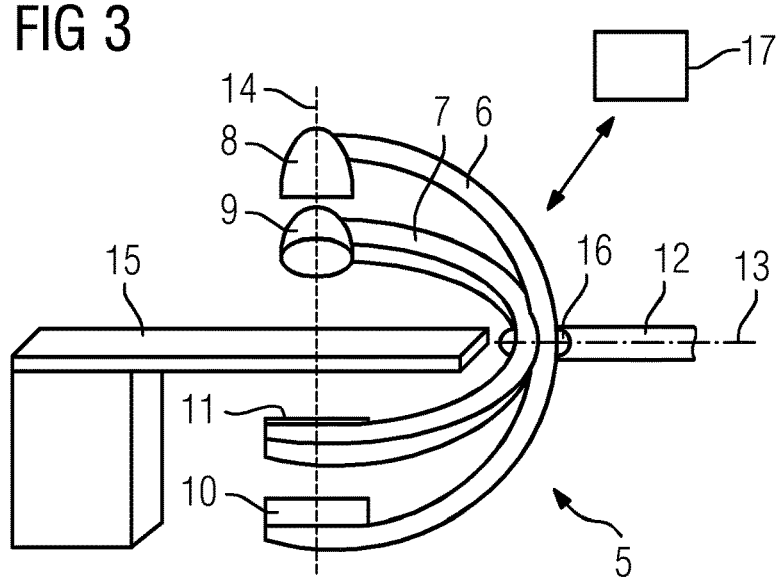
FIG. 3 shows a biplanar x-ray device.

FIG. 3 finally shows a schematic representation of a schematic diagram of one embodiment of a biplanar x-ray device 5, which has two C-arms 6, 7 that each support a recording arrangement. The recording arrangements each have an x-ray emitter 8, 9 and an x-ray detector 10, 11. The C-arms 6, 7 are held using a stand 12, only indicated, and can be rotated about an axis of rotation 13, which determines the plane 14 in which the circular recording trajectory lies. Various adjusting devices can be provided in order to adjust the position of the C-arms 6, 7, so that the examination area of a patient positioned on a patient couch 15 can be recorded as required.

Adjusting device 16 incidentally allows the angular offset of the recording arrangements to be adjusted with respect to one another, for instance as in the above example to 100°.

Operation of the biplanar x-ray device 5 is controlled by the controller 17, which is embodied to carry out the method. To this end the controller 17 can in particular have a consistency metric determination unit and a registration unit and the fundamentally known reconstruction unit.

Although the invention has been illustrated and described in detail with the preferred exemplary embodiment, the invention is not restricted by the examples given and other variations can be derived therefrom by a person skilled in the art without departing from the protective scope of the invention.

The invention claimed is:

1. A method for reconstructing a three-dimensional image data record of an examination object from two-dimensional projection images recorded with a biplanar x-ray device, the method comprising:

recording projections of a patient by two recording arrangements of the biplanar x-ray device, the two recording arrangements displaced by an angle relative to one another and each including one x-ray emitter and one x-ray detector, the projections comprising simultaneous pairs of projection images recorded at the same time with the different recording arrangements;

performing image-based spatial registration of the recording arrangements with respect to one another for at least one part of the simultaneous pairs, the performing including:
  determining degrees of consistency based on a redundancy in the projection data of the simultaneous pairs of the projection images, and
  determining the registration parameters describing the registration of the recording arrangements by minimization of a consistency metric determined by totaling the degrees of consistency in an optimization;
reconstructing the three-dimensional image data record of the patient from the projection images as spatially registered; and
x-ray imaging the three-dimensional image data record of the patient.

2. The method as claimed in claim 1, wherein the degree of consistency is based on the Grangeat's relation.

3. The method as claimed in claim 1, wherein the degree of consistency is determined with an intermediate function produced as a result of Radon transformation and differentiation of the projection images, the degree of consistency being determined from the intermediate function values containing differences in redundant information.

4. The method as claimed in claim 1, further comprising selecting the angle between the projection directions of the recording arrangements from a range of 90° to 105°.

5. The method as claimed in claim 4 wherein selecting comprises selecting the angle from the range of 95° to 105°.

6. The method as claimed in claim 1, wherein the projection images are recorded covering a projection angular range of 180° plus an opening angle of the radiation field, wherein the projection directions of the recording arrangements are offset by an angle of half of the extent of the projection angular range and each recording arrangement records projection images covering in each case one half of the projection angular range.

7. The method as claimed in claim 1, wherein recording comprises acquiring the projection images with the biplanar x-ray device having C-arms supporting the recording arrangements.

8. The method as claimed in claim 1, wherein recording comprises recording the projection images as part of a dynamic measurement and/or a measurement susceptible to patient movement.

9. The method as claimed in claim 8, wherein recording comprises recording as part of the dynamic measurement where the dynamic measurement comprises a perfusion measurement.

10. The method as claimed in claim 8, wherein the degree of consistency of the projection images of the two recording arrangements registered by the registration parameters is also additionally used for movement correction and/or dynamic analysis.

11. A biplanar x-ray device comprising:
two recording arrangements configured to measure projections of a patient displaced by an angle relative to one another, the two recording arrangements each having an x-ray emitter and an x-ray detector; and
a controller configured to:
  perform image-based spatial registration of the recording arrangements with respect to one another based on determination of a degree of consistency based on a redundancy in the projection data of simultaneous pairs of the projections and determination of registration parameters describing the registration of the recording arrangements by minimization of a consistency metric determined by totaling the degrees of consistency in an optimization; and
  reconstruct a three-dimensional image data record of the patient from the projections as spatially registered.

12. The biplanar x-ray device as claimed in claim 11, wherein the controller is configured to determine the degree of consistency based on the Grangeat's relation.

13. The biplanar x-ray device as claimed in claim 11, wherein the controller is configured to determine the degree of consistency with an intermediate function produced as a result of Radon transformation and differentiation of the projection images, the degree of consistency being determined from the intermediate function values containing differences in redundant information.

14. The biplanar x-ray device as claimed in claim 11, further comprising C-arms supporting the recording arrangements.

15. A non-transitory computer readable data carrier, on which is stored a computer program having instructions executable by a controller, for image-based spatial registration between a pair of x-ray emitters and x-ray detectors, the computer readable data carrier comprising instructions for:
recording the projection images of a patient with the pair of the x-ray emitters and x-ray detectors;
determining degrees of consistency based on a redundancy in projection data of simultaneous sets of the projection images from the pair of the x-ray emitters and x-ray detectors,
determining the spatial registration parameters describing the registration of the pair of the x-ray emitters and x-ray detectors by minimization of a consistency metric determined by totaling the degrees of consistency in an optimization; and
reconstructing an image data record for x-ray imaging from the projection images and the spatial registration parameters.

16. The non-transitory computer readable data carrier of claim 15, wherein the instructions include basing the degrees of consistency on Grangeat's relation.

17. The non-transitory computer readable data carrier of claim 15, wherein the instructions include determining the degrees of consistency with an intermediate function produced as a result of Radon transformation and differentiation of the projection images, the degrees of consistency being determined from the intermediate function values containing differences in redundant information.

18. The non-transitory computer readable data carrier of claim 15, wherein the instructions further comprise selecting an angle between projection directions of the pair from a range of 90° to 105°.

19. The non-transitory computer readable data carrier of claim 18, wherein the instructions include recording the projection images covering a projection angular range of 180° plus an opening angle of the radiation field, wherein the projection directions of the recording arrangements are offset by an angle of half of the extent of the projection angular range and each recording arrangement records projection images covering in each case one half of the projection angular range.

20. The non-transitory computer readable data carrier of claim 15, wherein the instructions include recording the projection images as part of a dynamic measurement and/or a measurement susceptible to patient movement.

* * * * *